(12) United States Patent
Brånemark

(10) Patent No.: US 7,331,962 B2
(45) Date of Patent: Feb. 19, 2008

(54) FIXTURE

(75) Inventor: Per-Ingvar Brånemark, Mölndal (SE)

(73) Assignee: PIOS Biotech AB, Göteborg (SE)

( * ) Notice: Subject to any disclaimer, the term of this patent is extended or adjusted under 35 U.S.C. 154(b) by 0 days.

(21) Appl. No.: 10/540,085

(22) PCT Filed: Dec. 18, 2003

(86) PCT No.: PCT/SE03/02014

§ 371 (c)(1),
(2), (4) Date: Oct. 14, 2005

(87) PCT Pub. No.: WO2004/056284

PCT Pub. Date: Jul. 8, 2004

(65) Prior Publication Data

US 2006/0149262 A1    Jul. 6, 2006

(30) Foreign Application Priority Data

Dec. 19, 2002   (SE)   .................................  0203787

(51) Int. Cl.
*A61B 17/58*   (2006.01)
(52) U.S. Cl. ........................................................ 606/73
(58) Field of Classification Search ............... 606/60, 606/62, 64, 72, 73; 433/174
See application file for complete search history.

(56) References Cited

U.S. PATENT DOCUMENTS

| | | | | |
|---|---|---|---|---|
| 4,484,570 A | * | 11/1984 | Sutter et al. | 606/72 |
| 5,246,369 A | | 9/1993 | Poulmaire | |
| 5,725,581 A | * | 3/1998 | Br.ang.nemark | 606/73 |
| 5,993,450 A | * | 11/1999 | Worcel | 606/73 |
| 6,126,662 A | * | 10/2000 | Carmichael et al. | 606/72 |
| 6,203,324 B1 | | 3/2001 | Wils | |
| 6,461,160 B1 | | 10/2002 | Sutter | |
| 6,482,207 B1 | * | 11/2002 | Errico | 606/61 |
| 6,517,543 B1 | * | 2/2003 | Berrevoets et al. | 606/73 |
| 6,575,975 B2 | * | 6/2003 | Brace et al. | 606/69 |
| 6,660,008 B1 | * | 12/2003 | Foerster et al. | 606/72 |
| 2004/0204713 A1 | * | 10/2004 | Abdou | 606/71 |

FOREIGN PATENT DOCUMENTS

DE    197 05 571 A1    9/1998

* cited by examiner

*Primary Examiner*—Cardo C. Robert
*Assistant Examiner*—Nicholas Woodall
(74) *Attorney, Agent, or Firm*—The Maxham Firm

(57) ABSTRACT

A fixture having an anchoring portion and an application portion intended for connection to a prosthesis. The application portion has an outer end and an end connected to the anchoring portion. The application portion includes a flared part whose outer dimensions widen from the end of that part connected to the anchoring portion in a direction toward the outer end of the application portion. This flared part is elastically resilient transversely to the longitudinal direction of the fixture.

14 Claims, 2 Drawing Sheets

FIXTURE

FIELD OF INVENTION

The present invention relates to a so-called fixture which is anchored to bone tissue. The fixture is of a kind that includes an anchoring portion with which the fixture is anchored, and an application portion intended for connection with a prosthesis and having an outer end and an end which is connected with the anchoring portion.

BACKGROUND OF THE INVENTION

Fixtures of this kind are used in prosthesis surgery, wherein the prosthesis, parts of a prosthesis, or a prosthesis holder is/are anchored in the bone tissue of a person with the aid of one or more such fixtures. The fixtures may be used for different types of prosthesis and are of different sizes, said size depending on the type of prosthesis concerned. However, the fixtures according to the present invention are primarily intended for anchorage in tubular bone and may be used, for instance, in the reconstruction of joints, such as finger joints and hip joints. However, the invention is not restricted to these applications and may be applied to secure artificial limbs or other types of prosthesis to the bone tissue of a patient.

The fixture includes an anchoring portion and an application portion. The anchoring portion is secured in the bone tissue of a patient, by screwing said portion into a hole that has been predrilled in the bone tissue, for instance. The application portion is designed to enable it to be connected to prosthesis in a suitable fashion.

When the fixture anchoring hole is provided in the bone marrow in the longitudinal direction of a bone, the mouth of the hole is likely to be widened outwards due to the internal contour of the bone. Subsequent to having driven the fixture into said hole to the position intended, with the anchoring portion fully screwed into the bone material, the application portion will be located in said widened region, either completely or partially This results in the formation of a space or clearing between the fixture and the bone material. This is unsuitable both with respect to the stability of the anchorage and the healing process. It is therefore desirable to avoid the occurrence of such a space.

Seen against this background, an object of the present invention is to provide a fixture in which this drawback is eliminated, in other words a fixture in which the occurrence of a space or clearing between the fixture and the bone tissue at the application portion of said fixture is avoided.

SUMMARY OF THE INVENTION

This object is achieved in accordance with the invention by virtue of the application portion including a flared part whose outer dimensions widen from the end of said part connected to the anchoring portion, in a direction towards the outer end of the application portion, wherein said flared part is elastically resilient in a direction transversely to the longitudinal direction of the fixture.

Because the application portion includes a part that widens in the aforesaid manner, the fixture will essentially fill out the space that would otherwise arise. Moreover, as a result of the elastic resilience said flared part will adapt to the shape corresponded by the widening occurring at the outer end of the hole when anchoring the fixture. This eliminates the danger of healing problems caused by the presence of said space. Moreover, said part will be compressed and deformed as a result of the widening at the mouth of the hole. Said part is therewith tightened against the flared surface and thus locked. This is achieved because the stresses generated tend to force said part to return to its original shape. The resilient part thus creates its own seating against the surrounding tissue, resulting in a highly stable anchorage.

According to one preferred embodiment of the invention, the flared part is formed by an outer wall that surrounds a cavity which is open towards the outer end of the application portion and which is provided with through-penetrating slots that extend from the outer end of the application portion, such as to connect the cavity with the outside of the outer wall. As a result of the slots, said outer wall forms a number of tongue-like flaps whose free ends are able to spring inwards at the outer end of the application portion. The elastic resilience is therewith achieved in a constructively simple manner, wherewith the resilient part is well able to adapt to the shape of the widening at the mouth of the insertion hole.

According to a further embodiment of the invention, the anchoring portion includes a threaded part which functions to enable the fixture to be anchored by screwing the anchoring portion into the predrilled hole, said widening part having an outer contour which is rotationally symmetrically about the centre axis defined by the threaded part.

Screwing of the anchoring portion into bone tissue is the most usual method of securing the fixture. Consequently, the inventive fixture is of significant interest since it is of the kind that can be screwed into bone tissue. Moreover, the inventive design of the application portion is particularly purposeful when anchoring the fixture by screwing the same into bone tissue. Screwing of the fixture into bone tissue is also facilitated by the fact that the flared part, is rotationally symmetrical.

According to a further embodiment of the invention, the flared part has the form of a truncated cone. Since the widening occurring at the mouth of the insertion hole is generally conical in shape, the truncated form of the flared part provides an advantageous adaptation to the widened part of said hole. The conical shape is also most suitable when the fixture is anchored by screwing the same into bone material.

According to another preferred embodiment of the invention, the cone angle is 5°-12°, preferably 7°-9°, The cone angle will preferably be slightly larger than the corresponding cone angle of the widening part at the mouth of the insertion hole. However, it should not be too large, since the occurring resistance to deformation may then be excessively strong and make anchoring of the fixture difficult to achieve and cause harmfully large stresses to build-up in the prosthesis anchoring construction. The chosen angular range of the cone angle is such as to optimally balance these aspects in respect of the different applications that may be of interest. For example, a fixture intended for a finger joint will preferably have a cone angle of about 8°, which is the most purposeful angle with respect to these aspects.

According to another preferred embodiment of the invention, each slot defines an angle with the radial direction of the truncated cone. This means that the slot walls will extend obliquely through the outer wall when seen in cross-section. It also means that each slot will extend obliquely in the axial direction, seen in the peripheral direction. This inclination of the slots means that the deformation occurring when the resilient part is compressed will be uniform, such as to essentially retain a conical shape when the fixture is screwed in.

According to another advantageous embodiment, the slots slope rearwardly from within and outwards in relation to the direction in which the fixture is screwed in, this direction being defined by the threaded part of the anchoring portion.

Because the slots slope obliquely rearwards, the edge formed between the trailing wall of the slot and the outside of the cone when screwing in the fixture will be blunt, or obtuse, whereas the corresponding edge on the leading wall of the slot will be sharp, or acute.

Because the edge that leads when screwing in the fixture is blunt, there is less risk of said edge hooking fast into surrounding tissue material when screwing in the fixture. This means that the compressive deformation taking place when screwing in the fixture will not be disturbed by said edge hooking into surrounding tissue material. The danger that hooking of the leading edge into surrounding tissue will create a resistance to screwing-in the fixture is similarly reduced. The cone can be considered as being "stroked smoothly" by the surrounding tissue material when screwing in the fixture. On the other hand, the obliqueness of the cone has the reverse effect when unscrewing the fixture, since the slots then hamper unscrewing of the fixture. This reduces the danger of the fixture being unscrewed unintentionally, therewith making the anchorage more secure.

According to another preferred embodiment of the invention, the slots have an angle of 20°-40° at their axially and radially outer ends. This angle will preferably lie in the range of 27°-33°, where an angle of about 30° is the most suitable in many applications. An angle in the aforesaid range will cause the desired deformation to be as uniform and as harmonious as possible, and allow optimum adaptation to the contour of the surrounding tissue material to be achieved.

According to another preferred embodiment, the outer wall has a thickness of 0.3-1.0 mm, preferably a thickness of 0.5-0.7 mm.

The thickness of the outer wall will preferably be chosen so as to create a stable support against the surrounding tissue, on the one hand, and radial resilient compression of the parts situated between the slots, on the other hand. The aforesaid thickness range is believed to provide an optimum balance in respect of these aspects.

According to a further preferred embodiment, the fixture is made of titanium. Although the fixture can be made of some other suitable material, for instance polymeric material, composite material or other metals than titanium, titanium is the material most preferred. Titanium has been found to adhere to bone material by so-called osseointegration in the absence of those negative reactions that may often occur when implanting foreign material in body tissue. Titanium has the ability to interact with and be integrated in bone tissue on a molecular level, such that the titanium will coalesce with the bone tissue. A titanium fixture will therewith be anchored very securely.

The invention also relates to the use of the inventive fixture for securing a prosthesis in bone tissue.

The inventive use affords advantages of a kind corresponding to the advantages given above with respect to the inventive fixture and its preferred further embodiments.

The invention will now be described in more detail with reference to an advantageous embodiment of the inventive fixture and with reference to the accompanying drawings.

DESCRIPTION OF ADVANTAGEOUS EMBODIMENTS

Figure 1:
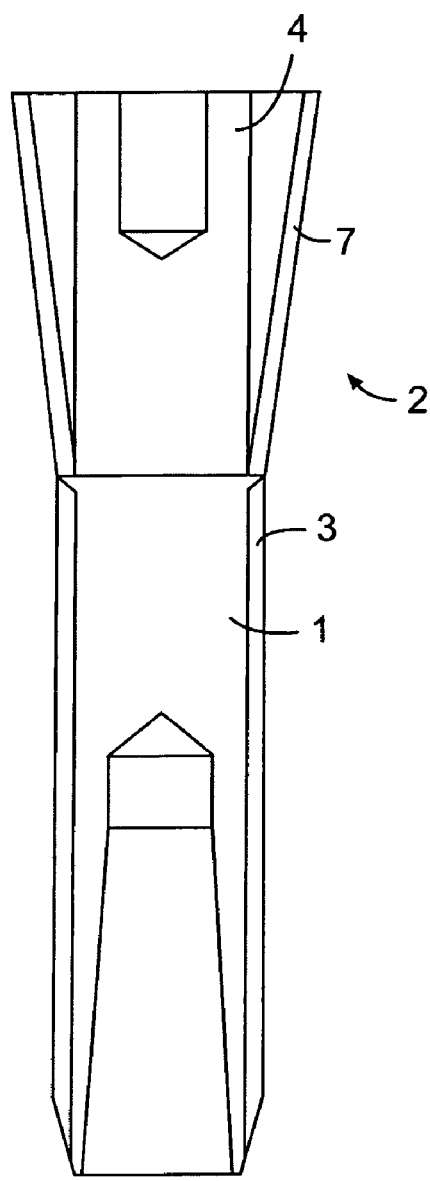
FIG. 1 is a longitudinally sectioned view of a fixture constructed in accordance with the invention.

FIG. 1 is a longitudinal sectional view of an inventive fixture. The illustrated fixture is intended for a finger joint and is dimensioned to this end. The fixture comprises an anchoring portion 1 and an application portion 2. The anchoring portion has a length of about 20 mm and the application portion a length of about 10 mm.

The anchoring portion includes an external screw thread 3 which is adapted to enable the fixture to be screwed into a hole predrilled in bone tissue. In the illustrated case, the thread is an M6 thread. The predrilled hole will preferably have a diameter that is slightly smaller than the inner diameter of the thread, i.e. a diameter of about 4.5 mm. The thread 3 extends along the full length of the anchoring portion 1.

Because the present invention is directed particularly to the design of the application portion 2, a detailed description of the design of the anchoring portion is believed to be unnecessary.

The application portion is comprised of a central body 4 which is circular-cylindrical along the major part of its extension. It includes a central bore 5 that has a diameter of 2.5 mm. The outer end of the body 4 has been given an hexagonal shape 6 (see FIG. 2) to enable the use of a corresponding tool for screwing-in the fixture.

An outer wall 7 is arranged around the central body 4. This outer body has the form of a truncated cone with the narrower end connected to the anchoring portion 1 of the fixture and the wider end connected to the outer end of the application portion, said truncated cone having roughly the same length as the central body 4.

There is formed between the central body 4 and the conical outer wall 7 a ring-shaped interspace that widens from the end adjacent the anchoring portion out towards the outer end of the application portion.

The outer wall has a thickness of 0.6 mm. The truncated cone has a smallest diameter of 5 mm, a largest diameter of 9 mm, and a length of about 10 mm. This corresponds to a cone angle of 8°.

Figure 2:
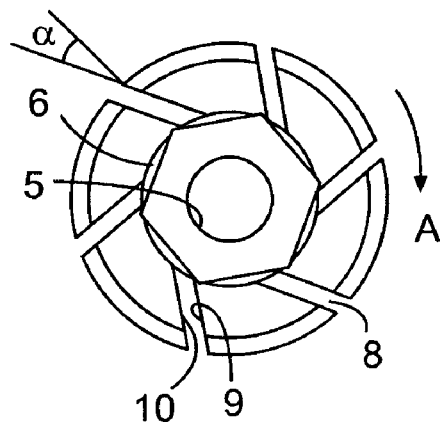
FIG. 2a is an end view similar to FIG. 2, with the direction of the slots reversed with respect to the direction of screwing-in rotation.

As will be seen from FIG. 2, six slots 8 are provided in the conical outer wall 7. Each slot is inclined in relation to the radial direction of the cone. The angle α between the radial direction and the slot direction is 30° at the radially and axially outermost end of the slot. Each slot extends between both ends of the cone and is therewith orientated obliquely to the barrel surface of the cone in the axial direction of said surface. Each slot has a width of 0.5 mm, i.e. a distance of 0.5 mm between two adjacent slot walls. The arrow A in FIG. 2 indicates the direction in which the fixture is screwed in. Seen in the direction in which the fixture is screwed in, the trailing slot wall 9 forms a blunt edge with the outer side of the cone, wherewith the angle of said edge is about 120° at the large end of the cone. A sharp edge having an angle of 60° is formed at the leading slot wall 10 at a corresponding position.

The modus operandi of the invention will now be described in more detail with reference to FIG. 3, which illustrates schematically and in side view an inventive fixture during screwing of the fixture into bone material adjacent a finger joint.

In this case, the fixture is screwed into the marrow cavity in the longitudinal direction of the bone. There is initially drilled in the marrow cavity a hole whose diameter corresponds approximately to the inner diameter of the thread. The fixture is self-tapping, so that the thread on the anchoring portion 1 will cut into the surrounding bone tissue and form a screw thread therein.

Figure 3:
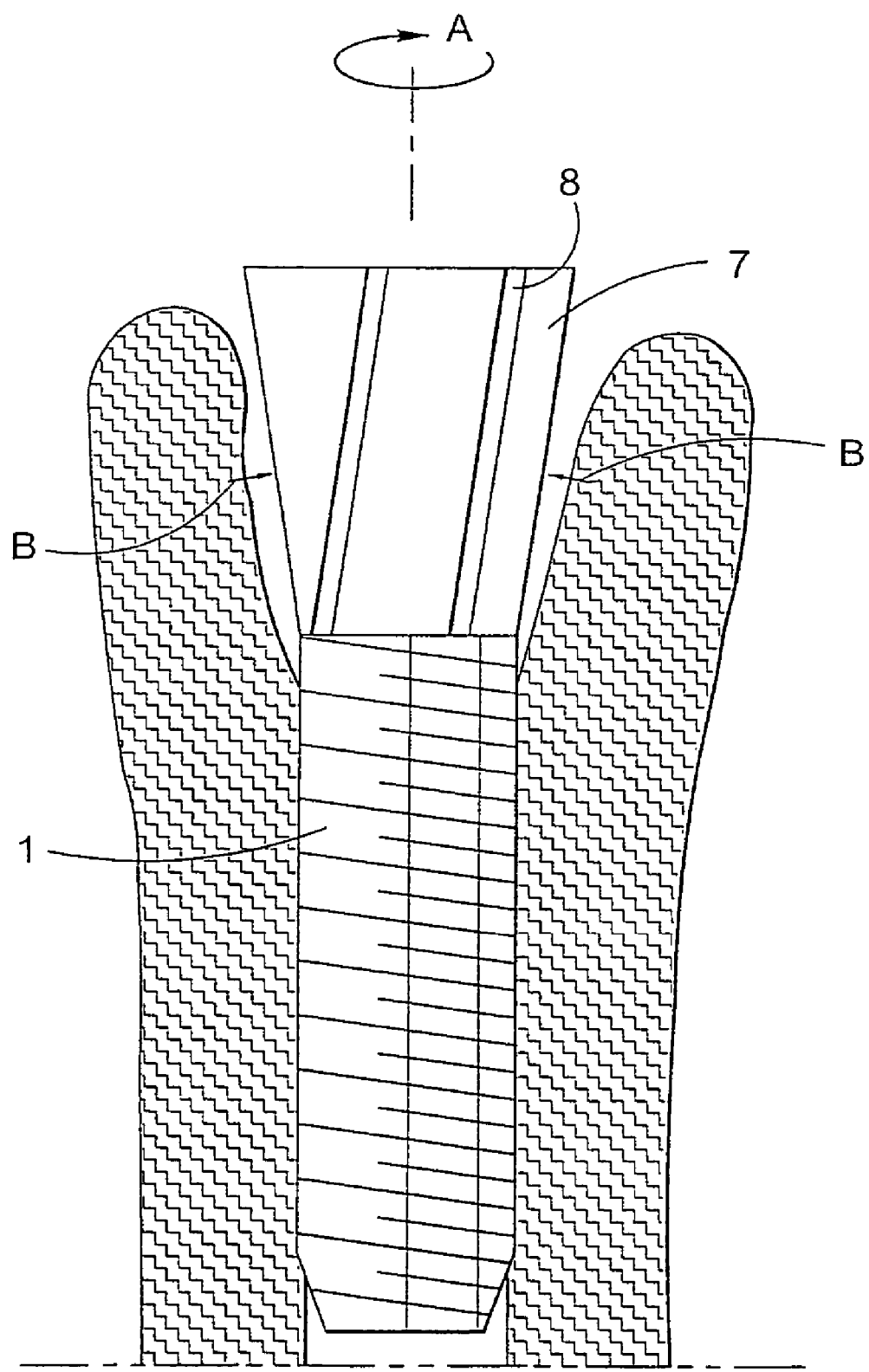
FIG. 3 illustrates schematically the principle according to which the fixture functions.

As will be seen from FIG. 3, the marrow cavity widens in a direction towards the end of the bone. The marrow cavity will thus have a generally conical extension at its mouth. The outer wall 7 on the application portion of the fixture has a cone angle which coincides essentially with the widening of the marrow cavity. The fixture has not been screwed fully home in the FIG. 3 illustration. Continued screwing of the fixture into the bone from the position shown in the figure will cause the outer wall 7 to approach the wall defining the widening of the marrow cavity and ultimately lie in abutment therewith. When the fixture is then screwed further into the bone, the conical outer wall 7 of the application portion will be compressed inwardly by the wall defining the marrow cavity, as indicated by the arrows B. This is made possible by the fact that the outer wall 7 is resilient as a result of the slots 8, as described above. This compression can result in a reduction in the cone diameter at the large end of the cone from 9 mm to less than 8 mm.

When the fixture is screwed fully home, its outer wall 7 will thus lie tightly against the conical expansion of the marrow cavity at the mouth of said cavity with a certain pressure. This eliminates the risk of inflammation or the like in the space that would otherwise have been formed in this region if the application portion of the fixture had had a typical cylindrical shape. The aforesaid abutment of the outer wall 7 with the conically widening marrow cavity results in an effective fixture support such as to provide a stable and secure fixture anchorage and also to increase its useful life.

Figure 2A:
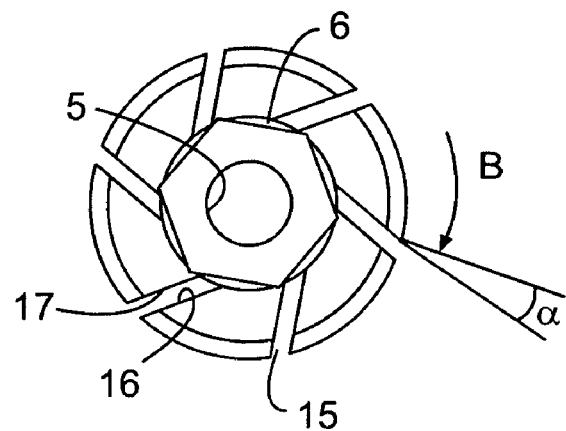

FIG. 2a shows the angle a reversed with respect to the direction of rotation indicated by arrow B. Slots 15 slope forwardly in the direction of screwing-in rotation, so that sharp edges 16 can engage the sides of the hole in the bone, and oblique edges 17 do not so engage the bone. Bore 5 and hexagonal end 6 remain the same as in FIG. 2. The angle $\alpha$ between the radial direction and the slot direction is also about 30°, ranging between 20° and 40°, as is true of the equivalent slot angle in FIG. 2.

The invention claimed is:

1. A fixture for anchorage in bone tissue, said fixture comprising:
    a fixture anchoring portion and an application portion shaped and configured for connection with a prosthesis, said anchoring portion including a screw-threaded part, wherein the application portion has an outer end and an end connected with said anchoring portion, said application portion being formed with a flared part whose outer dimensions widen from said end connected to said anchoring portion in a direction toward the outer end of said application portion, wherein said flared part is elastically resilient transversely to the longitudinal direction of said fixture;
    wherein said flared part has the form of a truncated cone and is formed by an outer wall that surrounds a cavity which is open toward the outer end of said application portion;
    wherein said outer wall is provided with through-penetrating slots which extend from said outer end of said application portion and which connect the cavity with the outside of said outer wall, wherein each said slot defines an angle $\alpha$ with the radial direction of the truncated cone; and
    wherein said slots slope rearwardly from the cavity to the outside of said outer wall in relation to the direction in which said fixture is rotated when screwing in said fixture, this direction being defined by said screw-threaded part.

2. The fixture according to claim 1, wherein said screw-threaded part functions to anchor the fixture when screwed into bone material and wherein said flared part has a rotationally symmetrical outer contour around the center axis defined by said screw-threaded part.

3. The fixture according to claim 1, wherein said truncated cone has a cone angle of 5°-12°.

4. The fixture according to claim 1, wherein said truncated cone has a cone angle of 7°-9°.

5. The fixture according to claim 1, wherein said slot angle $\alpha$ is 20°-40°, at the axially and radially outer end of respective slots.

6. The fixture according to claim 1, wherein said slot angle $\alpha$ is 27°-33°, at the axially and radially outer end of respective slots.

7. The fixture according to claim 1, wherein said outer wall has a thickness of 0.3-1.0 mm.

8. The fixture according to claim 1, wherein said outer wall has a thickness of 0.5-0.7 mm.

9. The fixture according to claim 1, wherein said fixture is made of titanium.

10. A fixture for anchorage in bone tissue, said fixture comprising:
    a fixture anchoring portion and an application portion shaped and configured for connection with a prosthesis, said anchoring portion including a screw-threaded part, wherein the application portion has an outer end and an end connected with said anchoring portion, said application portion being formed with a flared part whose outer dimensions widen from said end connected to said anchoring portion in a direction toward the outer end of said application portion, wherein said flared part is elastically resilient transversely to the longitudinal direction of said fixture;
    wherein said flared part has the form of a truncated cone having a cone angle of 5°-12°, said flared part being formed by an outer wall that surrounds a cavity which is open toward the outer end of said application portion;
    wherein said outer wall is provided with through-penetrating slots which extend from said outer end of said application portion and which connect the cavity with the outside of said outer wall, wherein each said slot defines an angle $\alpha$ with the radial direction of the truncated cone; and
    wherein said slots slope rearwardly from the cavity to the outside of said outer wall in relation to the direction in which said fixture is rotated when screwing in said fixture, this direction being defined by said screw-threaded part.

11. A fixture for anchorage in bone tissue, said fixture comprising:
    a fixture anchoring portion and an application portion shaped and configured for connection with a prosthesis, said anchoring portion including a screw-threaded part, wherein the application portion has an outer end and an end connected with said anchoring portion, said application portion being formed with a flared part whose outer dimensions widen from said end connected to said anchoring portion in a direction toward the outer end of said application portion, wherein said flared part is elastically resilient transversely to the longitudinal direction of said fixture;

wherein said flared part has the form of a truncated cone and is formed by an outer wall that surrounds a cavity which is open toward the outer end of said application portion;

wherein said outer wall is provided with through-penetrating slots which extend from said outer end of said application portion and which connect the cavity with the outside of said outer wall, wherein each said slot defines an angle α with the radial direction of the truncated cone; and wherein said slots slope forwardly from the cavity to the outside of said outer wall in relation to the direction in which the fixture is turned when screwing in the fixture, said direction being defined by the screw-threaded part.

12. The fixture according to claim 11, wherein said slot angle α is 20°-40°, at the axially and radially outer end of respective slots.

13. The fixture according to claim 11, wherein said slot angle α is 27°-33°, at the axially and radially outer end of respective slots.

14. A fixture for anchorage in bone tissue, said fixture comprising:

a fixture anchoring portion and an application portion shaped and configured for connection with a prosthesis, said anchoring portion including a screw-threaded part, wherein the application portion has an outer end and an end connected with said anchoring portion, said application portion being formed with a flared part whose outer dimensions widen from said end connected to said anchoring portion in a direction toward the outer end of said application portion, wherein said flared part is elastically resilient transversely to the longitudinal direction of said fixture;

wherein said flared part has the form of a truncated cone and having a cone angle of 5°-12°, said flared part being formed by an outer wall that surrounds a cavity which is open toward the outer end of said application portion;

wherein said outer wall is provided with through-penetrating slots which extend from said outer end of said application portion and which connect the cavity with the outside of said outer wall, wherein each said slot defines an angle α with the radial direction of the truncated cone; and wherein said slots slope forwardly from the cavity to the outside of said outer wall in relation to the direction in which the fixture is turned when screwing in the fixture, said direction being defined by the screw-threaded part.

* * * * *